(12) United States Patent
Ogura

(10) Patent No.: US 6,882,165 B2
(45) Date of Patent: Apr. 19, 2005

(54) CAPACITIVE TYPE SENSOR

(75) Inventor: Tsutomu Ogura, Tokyo (JP)

(73) Assignee: Yamatake Corporation, Tokyo (JP)

(*) Notice: Subject to any disclaimer, the term of this patent is extended or adjusted under 35 U.S.C. 154(b) by 0 days.

(21) Appl. No.: 10/625,080

(22) Filed: Jul. 22, 2003

(65) Prior Publication Data
US 2004/0080325 A1 Apr. 29, 2004

(30) Foreign Application Priority Data
Jul. 29, 2002 (JP) ........................ 2002-220198

(51) Int. Cl.[7] .............................................. G01R 27/26
(52) U.S. Cl. ........................................ 324/663; 361/303
(58) Field of Search ....................... 73/335.04; 324/663, 324/664, 689, 658, 670, 686, 699, 718; 361/303; 374/28

(56) References Cited

U.S. PATENT DOCUMENTS

| | | | |
|---|---|---|---|
| 4,773,935 A | 9/1988 | Uda et al. | |
| 6,222,376 B1 | 4/2001 | Tenney, III | |
| 6,445,565 B1 * | 9/2002 | Toyoda et al. | 361/303 |
| 6,628,501 B2 * | 9/2003 | Toyoda | 361/303 |
| 6,673,224 B2 * | 1/2004 | Shirai | 204/427 |
| 6,742,387 B2 * | 6/2004 | Hamamoto et al. | 73/335.04 |

FOREIGN PATENT DOCUMENTS

| | | |
|---|---|---|
| JP | 61-018850 A | 1/1986 |
| JP | 63-095347 A | 4/1988 |
| JP | 01-178858 A | 7/1989 |
| JP | 09-033470 A | 2/1997 |
| JP | 2001-004577 A | 1/2001 |

* cited by examiner

Primary Examiner—N. Le
Assistant Examiner—Walter Benson
(74) Attorney, Agent, or Firm—Frishauf, Holtz, Goodman & Chick, P.C.

(57) ABSTRACT

A capacitive type sensor includes a pair of electrodes disposed on a surface of an insulating substrate to face with each other, and a water vapor sensitive disposed between and in contact with the electrodes. These electrodes are each constituted by an electrically conductive material whose linear thermal expansion coefficient is less than that of the water vapor sensitive film and is substantially the same as that of the insulating substrate, and suppresses a swelling of the water vapor sensitive film caused when the sensor is placed in a high temperature/humidity environment, thus suppressing drift deterioration of the sensor.

11 Claims, 6 Drawing Sheets

CAPACITIVE TYPE SENSOR

BACKGROUND OF THE INVENTION

1. Technical Field

The present invention relates to a capacitive type sensor, and more particularly, to a capacitive type sensor capable of suppressing sensor's drift deterioration caused when the sensor is placed in a high temperature/humidity environment.

2. Related Art

Humidity sensors having a water vapor sensitive film of polymer material are generally classified into capacitive type sensors and resistive type sensors. Capacitive type humidity sensors are advantageous in that they have an excellent response to environment's humidity variation, a low output hysteresis with increasing/decreasing environment's humidity, and a less humidity-dependent water vapor sensitivity, and can make a measurement in a wide humidity/temperature range.

A parallel plate capacitive type humidity sensor, which is mainstream in capacitive type humidity sensors, generally comprises an insulating substrate; a lower electrode formed on the substrate; a water vapor sensitive film formed on the lower electrode and made of an electrically insulative, water vapor sensitive polymer material; and a porous upper electrode formed on the film. Thus, the lower electrode, water vapor sensitive film, and upper electrode are formed in layer in this order on the substrate. Lead wires are connected to the lower and upper electrodes, respectively.

When this humidity sensor is placed in an environment, water vapor (gas), i.e., water molecule, passes through the porous upper electrode to reach the inside of the water vapor sensitive film, to be absorbed therein. The water vapor absorption continues until the equilibrium of water vapor is established between the environment and the film. At the equilibrium, there occur water vapor absorption and desorption on the film, so that the resultant amount of water vapor in the film corresponds to the environment's relative humidity. On the other hand, the sensor's capacitance varies in proportion to an amount of water vapor absorbed in the film. Therefore, the environment's relative humidity can be measured based on the sensor's capacitance. To carry out a humidity measurement, an electrical output signal of the humidity sensor indicative of the sensor's capacitance is supplied to a humidity measuring device.

Prior to humidity measurement, the sensor's water vapor sensitive property is stored in the humidity measuring device. To this end, standard environments are prepared whose temperature is at 25 degree centigrade and whose relative humidities are individually at $x_0, x_1, ---, x_n$, for instance. With the sensor placed in the standard environments in sequence, sensor's capacitances $c_0, c_1, ---, c_n$ are measured by an impedance analyzer or the like. Then, a relationship between sensor's capacitance and environment's relative humidity, i.e., the sensor's water vapor sensitive property, is determined and stored in the humidity measuring device.

In an actual humidity measurement, the humidity measuring device receives an output signal from the humidity sensor placed in an environment whose humidity is to be measured. On the basis of the sensor output signal representative of the sensor's capacitance and the sensor's water vapor sensitive property representative of the relationship between capacitance and relative humidity, the humidity measuring device detects a relative humidity of the environment. For example, when the sensor output signal represents a capacitance $c_n$, a relative humidity $x_n$ is detected.

However, the parallel plate capacitive type sensor placed in a high temperature and humidity environment for long time tends to generate an electrical output signal representing a relative humidity higher than an actual humidity of the environment, resulting in an error in humidity measurement. For example, even if an actual relative humidity is at $x_n$, the sensor generates an inaccurate output signal $c_n+\Delta c$, so that an inaccurate relative humidity $x_n+\Delta x$ is detected based on the output signal $c_n+\Delta c$. Such phenomenon of an inaccurate output signal, representing a relative humidity higher than an actual relative humidity, being generated from a sensor placed in a high temperature and humidity environment is usually called as sensor's drift deterioration. According to the understanding of the present inventors, the drift deterioration is caused by a large swelling of the water vapor sensitive film of the sensor placed in a high temperature and humidity environment, as described later in detail.

To improve the measurement reliability of a parallel plate capacitive type sensor, the water vapor sensitive film is required to have an increased area size. Thus, the resultant sensor is large in size, failing to meet the demand of making the sensor compact.

This sensor is applicable to measurements for polarized formaldehyde, polarized acetone, polarized alcohol, etc., however, it entails problems of drift deterioration and upsizing also in that case.

SUMMARY OF THE INVENTION

An object of the present invention is to provide a capacitive type sensor capable of suppressing drift deterioration.

According to the present invention, there is provided a capacitive type sensor having first and second electrodes, a gas sensitive film provided between the electrodes, and an insulating substrate that supports the electrodes and the gas sensitive film thereon. The first and second electrodes are fixed on a surface of the insulating substrate to face each other, and each have a linear thermal expansion coefficient that is less than that of the gas sensitive film and substantially the same as that of the insulating substrate.

When the capacitive type sensor is placed in an environment, a gas present in the environment is absorbed by the gas sensitive film, and the sensor has a capacitance corresponding to an amount of gas absorbed in the film. Thus, a measurement regarding the environmental gas can be made based on the sensor's capacitance. Under a high temperature/high-density gas concentration environment, the gas sensitive film attempts to swell. However, the swelling (i.e., a volumetric increase due to thermal expansion and gas absorption) of the gas sensitive film is suppressed by the first and second electrodes fixed on a surface of the insulating substrate on both sides of the gas sensitive film and having a linear thermal expansion coefficient smaller than that of the film, whereby the sensor's drift deterioration attributable to the swelling of the gas sensitive film is suppressed.

Preferably, the gas sensitive film is a water vapor sensitive film, and the capacitive type sensor has its capacitance varying depending on an amount of water vapor absorbed in the water vapor sensitive film.

More preferably, the water vapor sensitive film has a linear thermal expansion coefficient equal to or greater than $2\times10^{-5}$ per degree centigrade, and the insulating substrate and the first and second electrodes each have a linear thermal expansion coefficient equal to or less than $1\times10^{-5}$ per degree centigrade.

With these two preferred embodiments, the environment's relative humidity can be measured based on the sensor's capacitance, and the sensor's drift deterioration attributable to the swelling of the water vapor sensitive film can be suppressed.

Preferably, the first and second electrodes each have a thickness falling within a range from 1 $\mu$m to 11 $\mu$m inclusive. With this preferred embodiment, the thickness of each electrode is made equal to or greater than an allowable lower limit determined from the viewpoint of improving the reliability in sensor operation, and at the same time is made equal to or less than an allowable upper limit determined from the viewpoint of reducing the hysteresis of sensor output.

Preferably, a face-to-face distance between the first and second electrodes falls within a range-from 0.5 $\mu$m to 5 $\mu$m inclusive. With this preferred embodiment, the face-to-face distance is made equal to or less than an allowable upper limit determined from the viewpoint of improving the reliability in sensor operation and made equal to or greater than an allowable lower limit determined from the viewpoint of preventing a failure in fabrication of the water vapor sensitive film.

Preferably, the capacitive type sensor further comprises an upper water vapor sensitive film formed on the first and second electrodes and the water vapor sensitive film, and a shielding film is formed in the upper water vapor sensitive film. With this preferred embodiment, a measurement error is eliminated that may be caused by capacitors formed between the upper water vapor sensitive film and the electrodes.

Preferably, the first and second electrodes are joined to the surface of the insulating substrate. With this preferred embodiment, the fixing strength of the electrodes to the insulating substrate increases.

DETAILED DESCRIPTION

Figure 1:
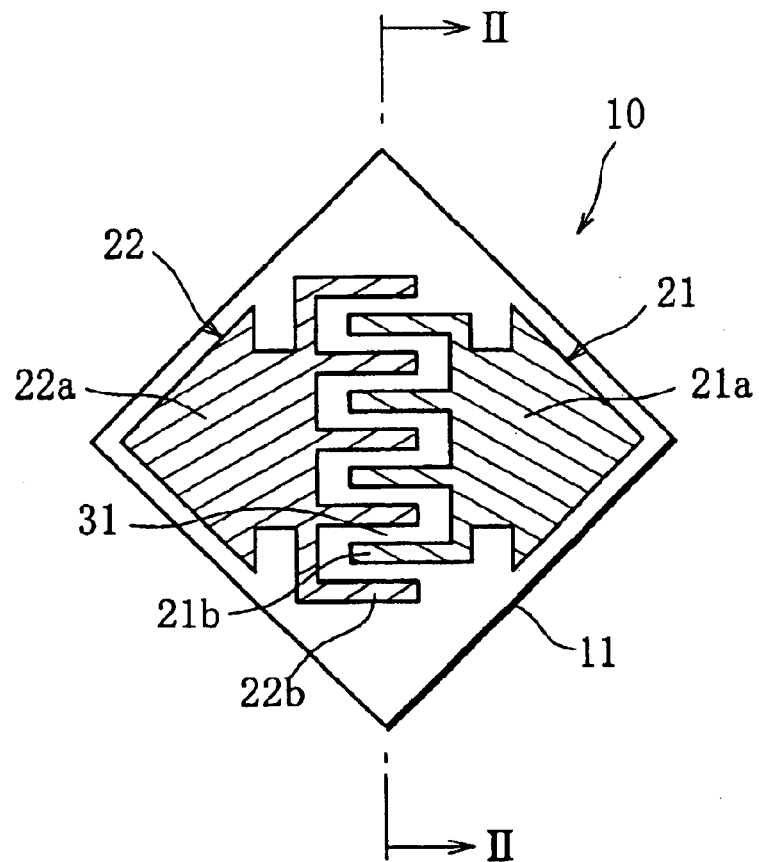
FIG. 1 is a plan view of a capacitive type sensor according to a first embodiment of the present invention.

First, the inventive concept of this invention will be described.

A capacitive type sensor is provided with a water vapor sensitive film generally constituted by a skelton part and a free volume part. The skelton part is formed by subjecting a polymer material to polycondensation, and the free volume part is distributed three-dimensionally in the skelton part in the form of micropores. When the sensor is placed in an environment, water vapor (gas) present in the environment moves in and out of the water vapor sensitive film, and as a result, water vapor whose amount corresponds to the environment's relative humidity is absorbed in the film.

According to the understanding of the present inventors, the phenomenon of water vapor being absorbed in a water vapor sensitive film is a phenomenon in which water vapor is caught in the free volume part of the water vapor sensitive film, and an amount of water vapor corresponding to the environment's relative humidity is absorbed in the free volume part when the equilibrium of water vapor is established between the environment and the sensor.

As mentioned previously, the parallel plate capacitive type sensor is comprised of a lower electrode, a water vapor sensitive film, and an upper electrode that are formed in layer in this order on an insulating substrate. When the sensor is placed in a high temperature and humidity environment, a swelling occurs in the water vapor sensitive film. With the swelling of the water vapor sensitive film, the volumetric ratio of the free volume part in the film increases, and the amount of water vapor absorbed in the free volume part becomes greater than that found prior to the occurrence of the swelling. To be noted, the absorbed water vapor is partly clustered, and the sensor's capacitance becomes larger by the capacitance of the clustered water. The clustered water remains staying in the free volume part even after the sensor is taken out from the high temperature and humidity environment. As a result, in the next humidity measurement, the output signal of the sensor represents a relative humidity higher than an actual relative humidity of the environment. In other words, the drift deterioration of the sensor is caused.

The present inventors reached a conclusion that, in the parallel plate capacitive type sensor, noticeable drift deterioration is caused mainly due to a large swelling of the water vapor sensitive film provided between upper and lower electrodes of the sensor, and have created the present invention based on the recognition that the drift deterioration can be suppressed by suppressing the swelling of the water vapor sensitive film.

Specifically, the capacitive type sensor of this invention comprises a first electrode, a second electrode, and a water vapor sensitive film (more generally, a gas sensitive film) that are provided on an insulating substrate in such a manner that the water vapor sensitive film is sandwiched between the electrodes from both sides of the film as viewed in plan, and the first and second electrodes are fixed to the insulating substrate. Each electrode is constituted by an electrically conductive material whose linear thermal expansion coefficient is less than that of a polymer material constituting the water vapor sensitive film and is substantially the same as that of a material constituting the insulating substrate.

With the capacitive type sensor having the above construction, the swelling of the water vapor sensitive film of the sensor placed in a high temperature and humidity environment is forcibly suppressed by the first and second electrodes closely provided on both sides of the film and accompanying a smaller thermal expansion. On the other hand, a positional relation between the electrodes and the insulating substrate is kept unchanged since the substrate accompanies substantially the same thermal expansion as that of the electrodes.

Basically, the capacitive type sensor of this invention has been created on the basis of the aforementioned inventive concept, whereas the below-mentioned capacitive type sensors according to preferred embodiments of this invention are designed also for easy sensor fabrication, improved reliability in sensor operation, etc.

In the following, a capacitive type sensor according to a first embodiment of this invention will be described with reference to FIGS. 1 and 2.

The capacitive type sensor of this embodiment comprises an insulating substrate 11 that is formed into a square shape as viewed in plan, and first and second electrodes 21, 22 that are fixed on a surface 11a of the substrate 11. The electrodes 21, 22 are disposed to face each other. The first electrode 21 comprises a first electrode body 21a extending from a corner of the substrate 11 toward a central part thereof, and a plurality of, e.g., four first comb-electrode (interdigital finger electrode) portions 21b formed integrally with the first electrode body 21a and extending from an inner end face of the first electrode body 21a to a central part of the substrate 11. Similarly, the second electrode 22 comprises a second electrode body 22a extending from a counter corner of the substrate 11 toward a central part thereof, and a plurality of, e.g., five second comb-electrode portions 22b formed integrally with the second electrode body 22a and extending from an inner end face of the second electrode body 22a toward a central part of the substrate 11. The first and second electrode bodies 21a, 22a each have a composite shape of triangle and rectangular sections. The first and second com-electrode portions 21b, 22b are alternately disposed with a predetermined face-to-face distance d therebetween, thus constituting a comb electrode structure (interdigital structure).

The capacitive type sensor 10 further comprises a water vapor sensitive film (more generally, a gas sensitive film) 30 that is provided on the surface 11a of the insulating substrate 11 so as to cover the electrodes 21, 22. The water vapor sensitive film 30 is comprised of a first water vapor sensitive film 31 arranged around and between the first and second comb-electrode portions 21b, 22b in contact therewith, and a second water vapor sensitive film (upper water vapor sensitive film) 32 that is provided on the upper surfaces of the electrodes 21, 22 and of the first water vapor sensitive film 31. The first and second water vapor sensitive films 31, 32 are formed integrally with each other. A plurality of (eight in the illustrated embodiment) vertically arranged capacitors C are formed on the substrate 11 by the first water vapor sensitive film 31 and the comb-electrode portions 21b, 22b.

Lead wires (not shown) are connected at their one ends with the electrode bodies 21a, 22a by using conductive adhesive, for instance. When measuring environment's relative humidity (more generally, when making a measurement regarding a gas present in an environment) by use of the capacitive type sensor 10, the lead wires are connected at their other ends with an impedance analyzer (not shown) or the like.

The following is a description of materials used to constitute the capacitive type sensor 10.

The insulating substrate 11 is constituted by an electrically insulating material, which may be any material so long as it has a linear thermal expansion coefficient that is substantially the same as that of a material constituting the electrodes 21, 22 and less than that of a material constituting the water vapor sensitive film 30. For instance, the material for the substrate 11 is selected from a group consisting of glass; quartz; silicon; ceramics such as silicon nitride, aluminum nitride, zirconia, and sialon (e.g., a reacted mixture of SiN, $SiO_2$, $Al_2O_3$ and AlN); and sapphire. Among them, a glass substrate is suitable for the insulating substrate 11 for the reason that it is low-priced, easy to machine, etc.

The water vapor sensitive film 30 may be constituted by any material so long as it is electrically insulative and water vapor sensitive. For example, a material for the film 30 is selected from a group consisting of a crosslinked polymer material; and an organic polymer material such as polyimide, polysulfone, polyethersulfone, polyetherimide, polyether, polyamide-imide, polyphenylene oxide, polycarbonate, polymethyl methacrylate, polybutylene terephthalate, polyethylene terephthalate, polyethyletherketon, polyetherketon, cellulose acetate butyl, cellulose acetate. Among them, crosslinked polyimide is suitable as a material for the water vapor sensitive film 30 since it is hardly deteriorated even under a corrosive environment and is excellent in long-term stability of water vapor sensitive property.

The first and second electrodes 21, 22 serve to forcibly suppress a swelling of the water vapor sensitive film 30, especially of the first water vapor sensitive film 31. To this end, the electrodes 21, 22 are constituted by an electrically conductive material whose linear thermal expansion coefficient is less than that of the water vapor sensitive film 30 and is substantially the same as that of the insulating substrate 11. The linear thermal expansion coefficient of a material for the water vapor sensitive film 30 is generally equal to or larger than $2 \times 10^{-5}$ per degree centigrade, and the linear thermal expansion coefficient of a material for the insulating substrate 11 is generally equal to or less than $1 \times 10^{-5}$ per degree centigrade. As a material for the electrodes 21, 22, therefore, an electrically conductive material having a linear thermal expansion coefficient equal to or less than $1 \times 10^{-5}$ per degree centigrade is selected from a group consisting of Si, SiC, GaAs, and polysilicon, for instance. Among them, Si is suitable as a material for the electrodes 21, 22 since it is easy to manufacture and easily obtainable.

From the viewpoint of improving the reliability of sensor operation, reducing the hysteresis of sensor output, and preventing a failure in formation of the water vapor sensitive film 30, the thickness of and the distance between the electrodes 21, 22 of the capacitive type sensor 10 are set to values falling within predetermined ranges, respectively.

Figure 2:
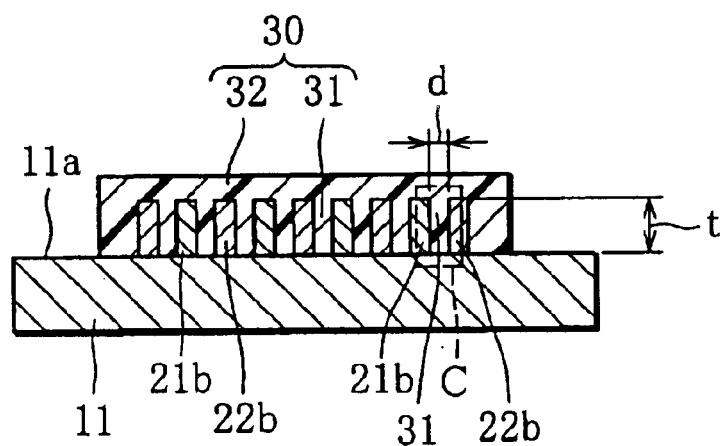
FIG. 2 is a sectional view of the capacitive type sensor taken along line II—II in FIG. 1.

More specifically, the thickness of the electrodes 21, 22 (especially, the thickness t of the comb-electrode portions 21b, 22b) is set to a value within a range from 1 $\mu$m to 11 $\mu$m, and the distance between the electrodes 21, 22 (especially, the face-to-face distance d between the comb-electrode portions 21b, 22b that cooperate with the first water vapor sensitive film 31 to form vertically arranged capacitors C shown by dotted lines in FIG. 2) is set to a value falling within a range from 0.5 $\mu$m to 5 $\mu$m. These suitable ranges are determined by the following reasons.

When setting the electrode thickness t to be less than 1 $\mu$m and/or when setting the face-to-face distance d to be larger than 5 $\mu$m, the vertically arranged capacitor C has an excessively small capacitance which in turn decreases the signal strength of the capacitive type sensor 10. This significantly lowers the reliability of sensor's capacitance value (i.e., the environment's relative humidity) measured by an impedance analyzer. For a relative humidity measurement with accuracy in the order of 1%, it is necessary to set the thickness t at a value equal to or larger than 1 $\mu$m and the face-to-face distance d at a value equal to or less than 5 $\mu$m.

On the other hand, when setting the face-to-face distance d of the electrodes to be less than 0.5 $\mu$m, difficulties will be encountered in filling a material between the comb-electrode portions 21b, 22b for the formation of the water vapor sensitive film 31 and in sufficiently accomplishing the subsequent crosslinking polymerization. This makes it difficult to form the water vapor sensitive film 31 with proper water vapor sensitivity. In other words, faulty products may be produced at a high rate.

When setting the electrode thickness t to be larger than 11 $\mu$m, absorption and desorption rates of water vapor in and out of the water vapor sensitive film 31 are lowered. As a result, the hysteresis characteristic of the sensor output is significantly deteriorated, to significantly lower the reliability of measured values.

Next, an exemplified method for manufacturing the capacitive type sensor 10 will be explained with reference to FIGS. 3–5.

First, a joined substrate is prepared that comprises an insulating substrate 11 and an electrically conductive substrate joined thereto. As the joined substrate, a commercially available SOI (silicon on insulator) substrate may be used that is comprised of a glass substrate and an Si wafer joined to one surface of the glass substrate, for instance.

Figure 3:
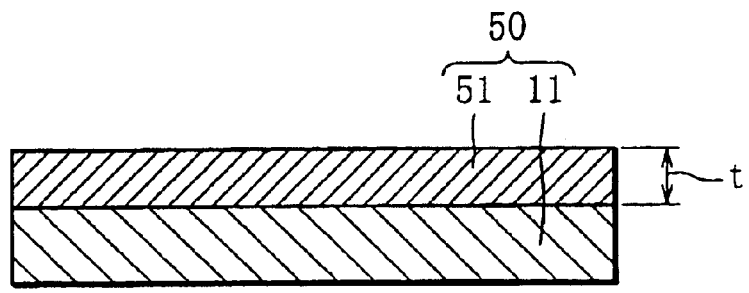
FIG. 3 is a sectional view of a starting substrate used for the fabrication of the capacitive type sensor shown in FIGS. 1 and 2.

Then, the conductive substrate is subject to polishing or etching to thereby fabricate an electrically conductive thin film 51 of a predetermined thickness t, whereby a starting substrate 50 shown in FIG. 3 is obtained. Next, the conductive thin film 51 is subject to photolithography and etching or subject to ICP (inductively coupled plasma) etching, thereby forming the first and second electrodes 21, 22 on the insulating substrate 11 as shown in FIG. 4.

Next, a material for water vapor sensitive film is filled in between the first and second electrodes 21, 22, thus forming the first water vapor sensitive film 31. Further, by using the same material, the second upper water vapor sensitive film 32 is formed on the electrodes 21, 22 and the first water vapor sensitive film 31.

Specifically, a resin liquid made of a suitable polymer material and prepared to have a proper viscosity is applied, as a material for water vapor sensitive film, between and around the first and second electrodes 21, 22 and also applied onto the electrodes by using a spincoat method. Thereafter, the resultant product is subject to heat treatment for drying and crosslinking polymerization of the resin, thus obtaining the water vapor sensitive film 30.

Finally, the water vapor sensitive film 30 on the electrodes 21, 22 is partly removed to expose part of surfaces of the bodies of the electrodes 21, 22 to which lead wires are individually connected, whereby the capacitive type sensor 10 is obtained.

In the following, a capacitive type sensor according to a second embodiment of this invention will be explained with reference to FIG. 6 which is a sectional view similar to FIG. 2 showing the capacitive type sensor 10 taken along line II—II in FIG. 1.

The capacitive type sensor 10A of the second embodiment contemplates improving the accuracy of a relative humidity measurement effected based on sensor's capacitance. This sensor 10A is different in construction from the capacitive type sensor 10 shown in FIGS. 1 and 2 in that it comprises a shielding film 40 embedded in the second humidity sensitive film (upper humidity sensitive film) 32, but is basically the same in construction as the capacitive type sensor 10 in other respects.

Figure 6:
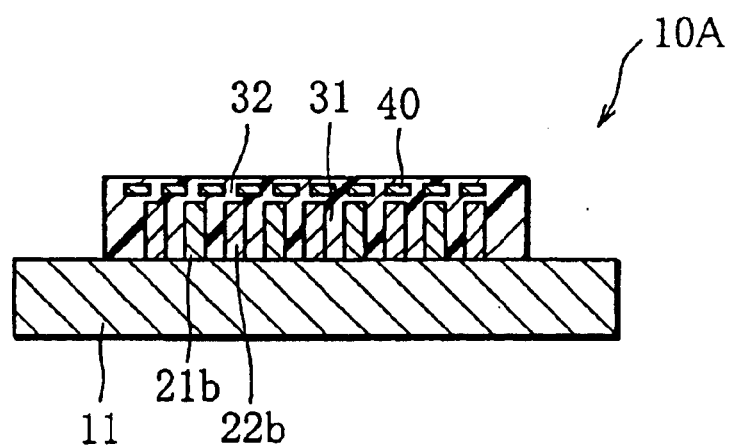
FIG. 6 is a sectional view of a capacitive type sensor according to a second embodiment of this invention.

The shielding film 40 is made of an electrically conductive material having a porous structure or a mesh structure, and is embedded in the upper water vapor sensitive film 32 at a location above and near the comb-electrode portions 21b, 22b of the first and second electrodes 21, 22, as shown in FIG. 6.

In the capacitive type sensor 10 of the first embodiment shown in FIGS. 1 and 2, vertically arranged capacitors are formed by the water vapor sensitive film 31 and the comb-electrode portions 21b, 22b, and in addition, horizontally arranged capacitors are formed by the upper water vapor sensitive film 32 and the comb-electrode portions 21b, 22b. For this reasons, the capacitive type sensor 10 generates the output that reflects both the capacitance of the vertically arranged capacitors and the capacitance of the horizontally arranged capacitors.

Contrary to this, in the capacitive type sensor 10A of the second embodiment, the shielding film 40 serves to prevent the upper water vapor sensitive film 32 and the comb-electrode portions 21b, 22b from forming horizontally arranged capacitors. As a result, the capacitive type sensor 10A generates the output that only reflects the capacitance of the vertically arranged capacitors formed by the water vapor sensitive film 31 and the comb-electrode portions 21b, 22b, thus improving the accuracy of the relative humidity measurement based on the sensor's capacitance, i.e., the sensor output.

Figure 4:
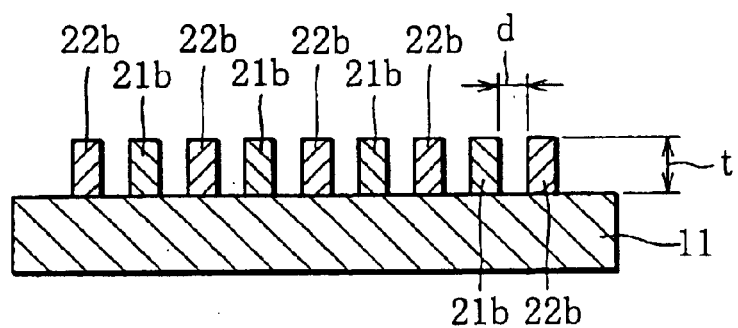
FIG. 4 is a sectional view showing a state where electrodes are formed on the starting substrate shown in FIG. 3.
Figure 5:
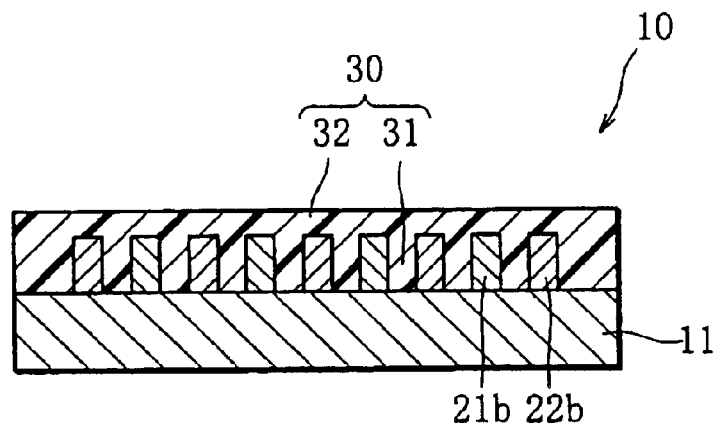
FIG. 5 is a sectional view showing a state where a water vapor sensitive film is formed.

The capacitive type sensor 10A can be fabricated basically in the same manner as the capacitive type sensor 10 by means of fabrication processes shown in FIGS. 3–5. In the fabrication of the capacitive type sensor 10A, a shielding film 40 of porous or mesh structure having a thickness of several hundred angstroms to several thousand angstroms is formed on the upper water vapor sensitive film 32 shown in FIG. 5, and then an overcoat film is formed on the shielding film, for instance.

Figure 7:
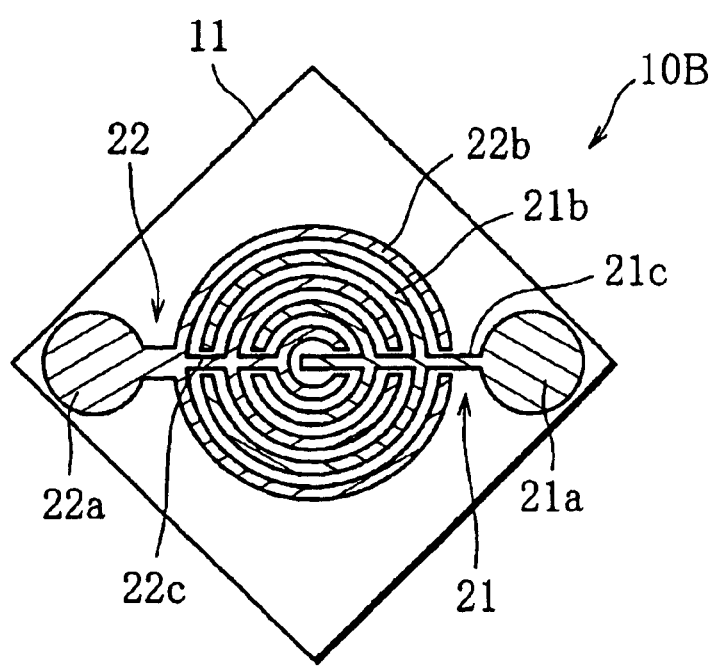
FIG. 7 is a plan view of a capacitive type sensor according to a third embodiment of this invention.

In the following, a capacitive type sensor according to a third embodiment of this invention will be explained with reference to FIG. 7.

As compared to the capacitive type sensor 10 of the first embodiment, the capacitive type sensor 10B of the third embodiment mainly differs in the shape of first and second electrodes 21, 22, but is the same in other respects.

The capacitive type sensor 10B comprises an insulating substrate 11 which is formed into a square planar shape, a first electrode 21 having a first electrode body 21a made of a circular plate and disposed at one corner of the insulating substrate 11, and a second electrode 22 having a second electrode body 22a made of a circular plate and disposed at the opposite corner of the substrate 11. As in the case of the sensor 10, the electrodes 21, 22 of the capacitive type sensor 10B are fixed on a surface of the substrate 11 and each have a thickness varying from 1 $\mu$m to 11 $\mu$m.

The first electrode 21 has a first straight electrode portion 21c extending from the first electrode body 21a toward the second electrode body 22a, and a plurality of, e.g., three first annular electrode portions 21b extending from the straight electrode portion 21c. Similarly, the second electrode 22 has a second straight electrode portion 22c extending from the second electrode body 22a toward the first electrode body 21a, and a plurality of, e.g., two second annular electrode portions 22b extending from the straight electrode portion 22c. The first and second annular electrode portions 21b, 22b are disposed alternately one another and coaxially with the center of the insulating substrate 11. As in the case of the comb-electrode portions 21b, 22b of the sensor 10, the first and second annular electrode portions 21b, 22b of the capacitive type sensor 10B face each other with a face-to-face distance varying from 0.5 μm to 5 μm.

The capacitive type sensor 10B comprises a water vapor sensitive film corresponding to the film 30 shown in FIG. 2, and lead wires individually connected to the electrode bodies 21a, 22a. The water vapor sensitive film is disposed between and in contact with the first and second annular electrode portions and cooperates with these electrode portions to constitute vertically arranged capacitors. This sensor 10B cooperates with an impedance analyzer, connected through the lead wires to the electrodes 21, 22, to make a measurement of the environment's relative humidity.

As with the case of the sensor 10, the electrodes 21, 22 of the capacitive type sensor 10B are each constituted by an electrically conductive material whose linear thermal expansion coefficient is less than that of the water vapor sensitive film and is substantially the same as that of the insulating substrate 11, thus suppressing the drift deterioration of the sensor 10B.

Figure 8:
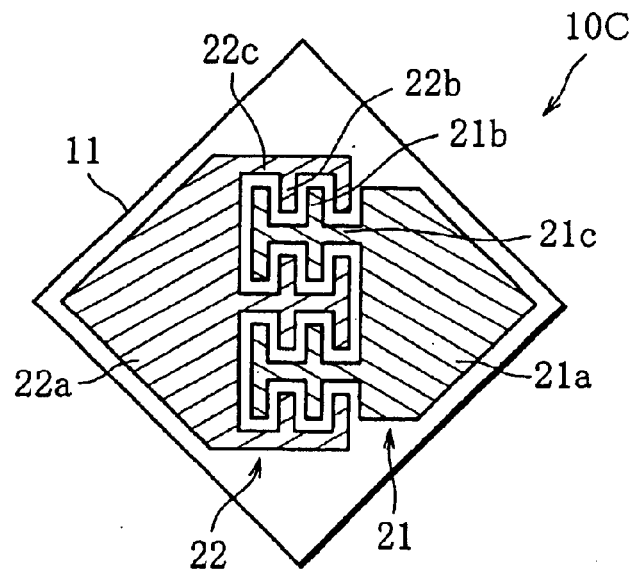
FIG. 8 is a plan view of a capacitive type sensor according to a fourth embodiment of this invention.

In the following, a capacitive type sensor according to a fourth embodiment of this invention will be explained with reference to FIG. 8.

As compared to the capacitive type sensor 10 of the first embodiment, the capacitive type sensor 10C of the fourth embodiment mainly differs in the shape of first and second electrodes 21, 22, but is the same in other respects.

The capacitive type sensor 10C comprises first and second electrodes 21, 22 fixed to an insulating substrate 11 to face each other. The first electrode 21 has a first electrode body 21a of a composite shape of triangle and rectangle sections, and one or more, e.g., two first straight electrode portions 21c extending from an inner end face of the first electrode body 21a toward a body 22a of the second electrode 22. A plurality of, e.g., two first toothed electrode portions 21b extend perpendicularly from each straight electrode portion 21c.

Similarly, the second electrode 22 has a second electrode body 22a of a composite shape, and a plurality of, e.g., three second straight electrode portions 22c extending from an inner end face of the second electrode body 22a toward the first electrode body 21a. A plurality of, e.g., two second toothed electrode portions 22b extend perpendicularly from each straight electrode portion 22c.

Each of the first straight and toothed electrode portions 21c, 21b is disposed to be adjacent to one or ones of the second straight and toothed electrode portions 22c, 22b with a face-to-face distance varying from 0.5 μm to 5 μm. A water vapor sensitive film is disposed between and in contact with adjacent ones of electrode portions 21c, 21b, 22c and 22b, and cooperates with the adjacent electrode portions to form vertically arranged capacitors.

In other respects, the capacitive type sensor 10C is the same as the sensor 10, and hence further explanations will be omitted.

Figure 9:
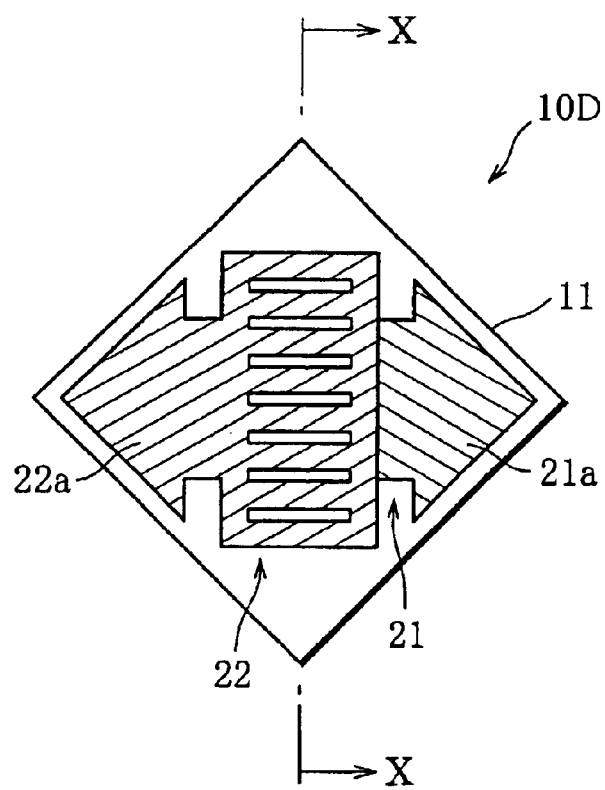
FIG. 9 is a plan view of a capacitive type sensor according to a fifth embodiment of this invention.
Figure 10:
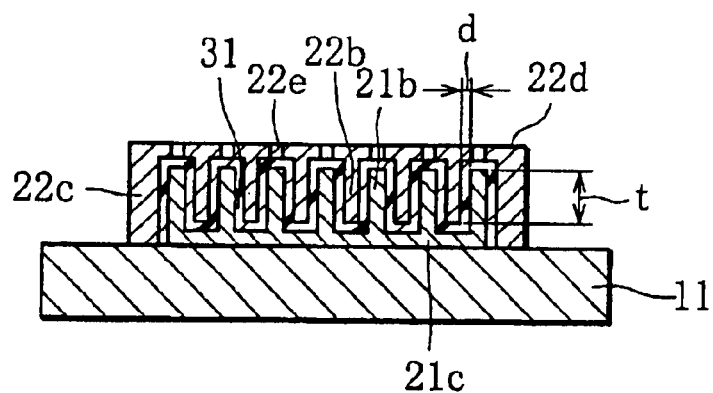
FIG. 10 is a sectional view of the capacitive type sensor taken along line X—X in FIG. 9.

In the following, a capacitive type sensor according to a fifth embodiment of this invention will be explained with reference to FIGS. 9 and 10.

As compared to the capacitive type sensor 10 of the first embodiment, the capacitive type sensor 10D of the fifth embodiment mainly differs in the construction of first and second electrodes 21, 22, but is the same in other respects.

The capacitive type sensor 10D comprises a first electrode 21 that has a first electrode body 21a and a lower electrode portion 21c extending from an inner end face of the first electrode body 21a toward a body 22a of the second electrode 22. The first electrode body 21a and the lower electrode portion 21c are fixed to an insulating substrate 11, and a plurality of, e.g., seven first toothed electrode portions 21b extend upward perpendicularly from an upper face of the lower electrode portion 21c. The first toothed electrode portions 21b are disposed at equal intervals and cooperate with the lower electrode portion 21c to form lower comb electrodes.

On the other hand, the second electrode 22 of the capacitive type sensor 10D includes the second electrode body 22a mentioned above and an upper electrode portion 22c extending from an inner end face of the second electrode body 22a toward the first electrode body 21a. The upper electrode portion 22c has an upper wall, and right and left side walls that are fixed at their bottom faces to a surface of the insulating substrate 11. A plurality of, e.g., six second toothed electrode portions 22b extend downward perpendicularly from the upper wall of the upper electrode portion 22c. The second toothed electrode portions 22b are disposed at equal intervals and cooperate with the upper electrode portion 22c to form an upper comb electrodes.

The upper and lower comb electrodes are alternately disposed with a face-to-face distance d varying from 0.5 μm to 5 μm, to constitute a comb electrode structure. A water vapor sensitive film corresponding to the film 31 shown in FIG. 2 is formed between the upper and lower comb electrodes, whereby a plurality of (in the illustrated example, fourteen) vertically arranged capacitors are formed.

Openings 22e are formed in the upper wall of the upper electrode portion 22c at locations right above the first toothed electrode portions 21b, so that water vapor moves through the openings 22e between the capacitive type sensor 10D and an environment where the sensor is placed, the water vapor being absorbed in and desorbed from the water vapor sensitive film.

In other respects, the capacitive type sensor 10D is the same as the sensor 10, and hence further explanations will be omitted.

EXAMPLE 1

A plurality of capacitive type sensors of Example 1, each corresponding to the sensor 10 shown in FIGS. 1 and 2, were fabricated as described below.

First, SOI substrates were prepared, each having a glass substrate serving as an insulating substrate 11, and an Si wafer joined to one surface of the glass substrate and serving as an electrically conductive substrate. Next, the Si wafers of the SOI substrates were subject to polishing, thus obtaining starting substrates 50 (refer to FIG. 3) provided with Si thin films that are different in thicknesses (electrode thickness t). The Si thin films of the starting substrates 50 were subject to ICP etching, whereby electrodes 21, 22 having comb-electrode portions 21b, 22b whose face-to-face distance was 5 μm were formed on the insulating substrate 11 (refer to FIG. 4). Polyimide-based resin liquid serving as a material for water vapor sensitive film was applied onto the electrodes 21, 22, and the resultant product was subject to thermal treatment at a temperature of 300 degree centigrade to promote crosslinking polymerization of the resin, thus forming a water vapor sensitive film 30 between and around the electrodes. The Si and the polyimide water vapor sensitive film had linear thermal expansion coefficients of $3.3 \times 10^{-6}$ per degree centigrade and $5 \times 10^{-5}$ per degree centigrade, respectively. Finally, those parts of the water vapor sensitive film 30 which covered electrode bodies 21a, 22a were partly removed, and lead wires of Cu were joined to the exposed electrode bodies with conductive adhesive, whereby the capacitive type sensors of Example 1 were fabricated that were different in electrode thickness t from one another.

After leaving the capacitive type sensors in a lower temperature and humidity environment at a temperature of 25 degree centigrade and a relative humidity of 10 percent, capacitances $C_1$ (pF) of these sensors were measured by using an LCZ meter under measurement conditions at a frequency of 100 kHz and an applying voltage of 1.0 volt. Subsequently, the capacitive type sensors were left for 20 hours in a higher temperature and humidity environment at a temperature of 40 degree centigrade and a relative humidity of 90 percent, and were then returned to the just-mentioned lower temperature and humidity environment. Then, capacitors $C_2$ (pF) of the sensors were measured.

As mentioned previously, water vapor absorbed in the water vapor sensitive film of a capacitive type sensor is clustered while the sensor is placed in a higher temperature/humidity environment, and the clustered water remains staying in the film even after the sensor is returned to a lower temperature/humidity environment. Thus, the sensor's capacitance $C_2$, measured after the sensor is returned from a higher temperature/humidity environment to a lower temperature/humidity environment, is greater than the sensor's capacitance $C_1$ initially measured in the lower temperature/humidity environment. Hereinafter, the capacitance difference $(C_2-C_1)$ will be referred to as a water vapor sensitivity hysteresis of the capacitive type sensor.

Figure 11:
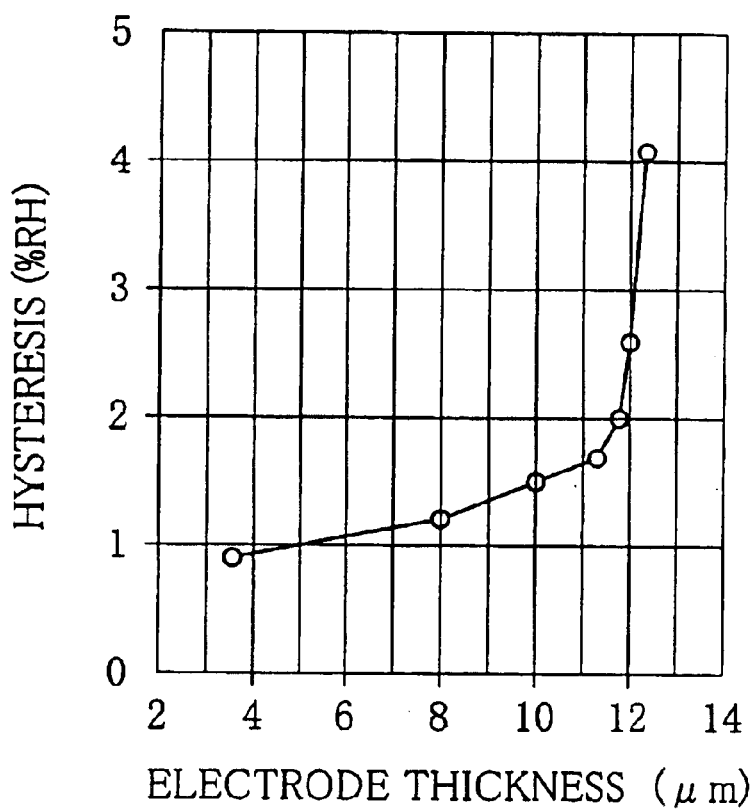
FIG. 11 is a graph showing a relationship between electrode thickness and hysteresis of sensor output in a capacitive type sensor according to Example 1.

FIG. 11 shows a relationship between electrode thickness t and water vapor sensitivity hysteresis that was determined based on the electrode thicknesses t and hysteresises of the capacitive type sensors of Example 1. As apparent from FIG. 11, the water vapor sensitivity hysteresis abruptly increases in a range of electrode thickness t grater than 11 μm, greatly deteriorating the reliability of values measured by the capacitive type sensor.

EXAMPLE 2

A number of capacitive type sensors of Example 2 (corresponding to the sensor 10 shown in FIGS. 1, 2) were fabricated in the same manner as the sensors of Example 1. In the fabrication of these sensors, the electrode thickness t remained constant at 5 μm, whereas the face-to-face distance d of comb-electrode portions 21b, 22b were varied in a range from about 0.3 μm to 5 μm. The distances d were at about 0.3 μm, 0.5 μm, 1 μm, 1.2 μm, 2 μm, 3 μm, 4 μm, and 5 μm.

Figure 12:
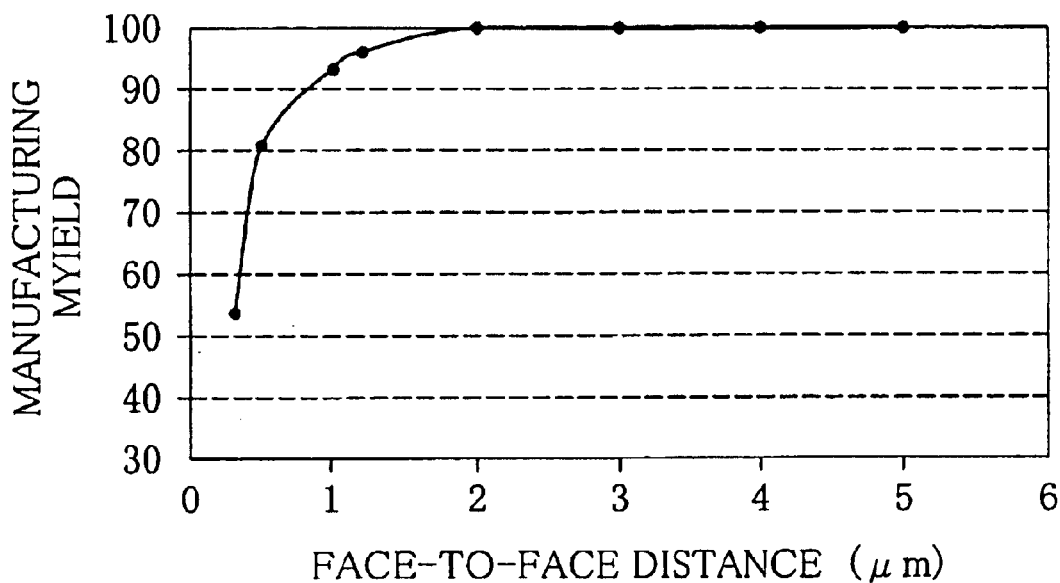
FIG. 12 is a graph showing a relationship between manufacturing yield of a capacitive type sensor according to Example 2 and face-to-face distance of electrodes.

The capacitive type sensors having been fabricated were divided into groups depending on the face-to-face distance d, and the sensors were divided into acceptable products without a failure in the water vapor sensitive film and faulty products with such a failure. Then, the fabrication yield for each sensor group was determined from a ratio of the number of acceptable products belonging to the sensor group to the total number of sensors belonging thereto). FIG. 12 shows relative fabrication yields for respective distances d, assuming that the fabrication yield of the sensors having the distance d of 3 μm is equal to 100.

As apparent from FIG. 12, the fabrication yield of capacitive type sensor abruptly decreases in a range where the face-to-face distance d is less than 0.5 μm.

EXAMPLE 3

A capacitive type sensor of Example 3, corresponding to the sensor 10A shown in FIG. 6, was fabricated by using an SOI substrate, and by using polyimide as a material for water vapor sensitive film. The capacitive type sensor was 5 μm in both the thickness and face-to-face distance of comb-electrode portions, and 3 μm in thickness of an upper water vapor sensitive film in which a shielding film made of Cr and having a thickness of 2000 angstroms was provided.

First to fifth standard environments were prepared that were at a temperature of 25 degree centigrade and at relative humidities of, e.g., 10%, 25%, 45%, 70% and 90%, respectively, for instance. Next, the capacitive type sensor of Example 3 was placed in the first standard environment, and the sensor's capacitance $C_{10}$ was measured. Subsequently, the sensor was left for 200 hours in a higher temperature/humidity environment at a temperature of 40 degree centigrade and a relative humidity of 90%, was returned to the first standard environment, and the sensor capacity $C_x$ was measured. Similar measurements were made in respect of the second through fifth environments, thus determining the sensor's capacitances shown by black circle marks in FIG. 13 and sensor's capacitances $C_x$ shown by black rectangular marks in FIG. 13.

Figure 13:
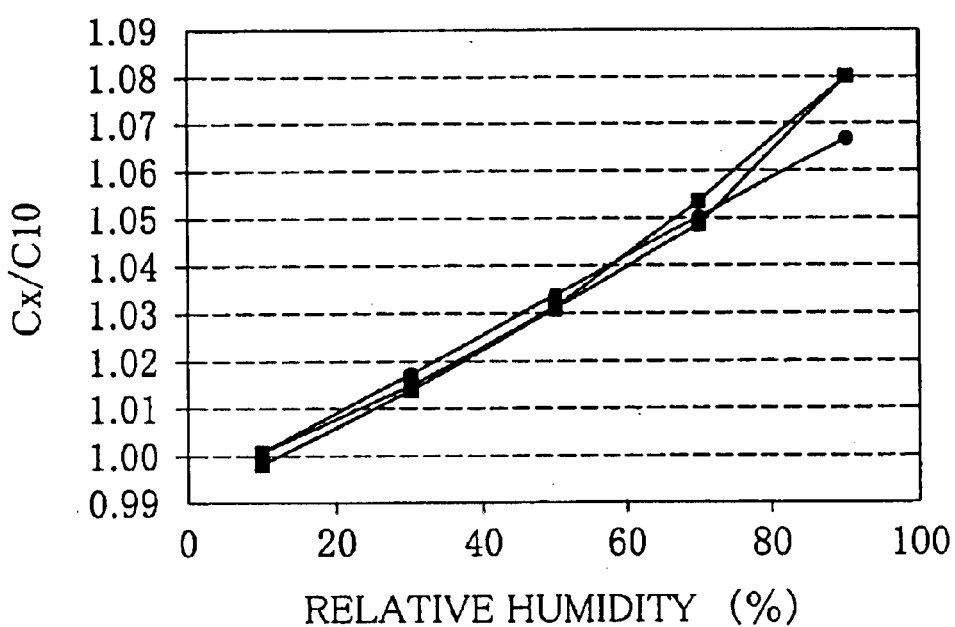
FIG. 13 is a graph showing a relationship between $C_x/C_{10}$ and relative humidity in a capacitive type sensor according to Example 3.

Ratios $C_x/C_{10}$ of the sensor's capacitances $C_x$ for the first to fifth environments to the capacitance $C_{10}$ were calculated, respectively. FIG. 13 shows a relationship between ratio $C_x/C_{10}$ and relative humidity. As apparent from FIG. 13, the ratio $C_x/C_{10}$ increases in proportion to the increasing relative humidity in a range where the relative humidity is less than about 70%. This indicates that the capacitive type sensor of Example 3 has an excellent linearity of the ratio $C_x/C_{10}$, so that only a small sensor's drift deterioration may be caused, even if the sensor is placed in a high temperature/humidity environment for long time.

As understood from the foregoing explanations, the capacitive type sensor of this invention can suppress a swelling of a water vapor sensitive film by arranging the film between and in contact with electrodes that are constituted by a material whose linear thermal expansion efficient is less than that of the water vapor sensitive film. This capacitive type sensor hardly causes drift deterioration even in a high temperature/humidity environment, and can output a highly reliable capacitance signal (humidity signal), thus being suitable for a humidity sensor.

The capacitive type sensor of this invention includes vertically arranged capacitors that make it possible to provide a large number of capacitors providing a large capacitance as a whole on a small-sized substrate as compared to a parallel plate type capacitor, so that the sensor can be made compact in size without lowering detection sensitivity.

The present invention is not limited to the foregoing preferred embodiments, and may be modified variously.

For instance, although a case has been explained in the embodiments where the capacitive type sensor is used as a humidity sensor for measuring the environment's humidity, the present invention is also applicable to a capacitive type sensor for detecting a gas that may be absorbed in and desorbed from a polymer film to thereby change the capacitance of the polymer film. In particular, the present invention that can suppress drift deterioration of a capacitive type sensor used under a high temperature/humidity environment is suitably applied to a technical field which requires an extremely high humid environment, such as fuel cell, planting facilities, and the like.

What is claimed is:

1. A capacitive type sensor comprising:
an insulating substrate;
first and second electrodes mounted on the insulating substrate to face each other; and
a gas sensitive film provided between the first and second electrodes and supported by the insulating substrate;
wherein the gas sensitive film has a linear thermal expansion coefficient of at least $2 \times 10^{-5}$ per degree centigrade;
wherein the first and second electrodes have a linear thermal expansion coefficient which is substantially the same as the linear thermal expansion coefficient of the insulating substrate and which is not more than $1 \times 10^{-5}$ per degree centigrade;
wherein said first and second electrodes each have a thickness from 1 $\mu$m to 11 $\mu$m, inclusive; and
wherein a face-to-face distance between said first and second electrodes is from 0.5 $\mu$m to 5 $\mu$m, inclusive.

2. The capacitive type sensor according to claim 1, wherein the gas sensitive film is a water vapor sensitive film, and a capacitance of the capacitive type sensor varies in accordance with an amount of water vapor absorbed by the water vapor sensitive film.

3. The capacitive type sensor according to claim 2, wherein:
the insulating substrate consists essentially of a material that is selected from the group consisting of glass, quartz, silicon, ceramics, and sapphire,
the water vapor sensitive film consists essentially of a material that is selected from the group consisting of a crosslinked polymer material, and an organic polymer material, and
the first and second electrodes each consists essentially of a material that is selected from the group consisting of Si, Sic, GaAs, and polysilicon.

4. The capacitive type sensor according to claim 2, further comprising:
an upper water vapor sensitive film provided on the first and second electrodes and the water vapor sensitive film;
wherein a shielding film is provided in the upper water vapor sensitive film.

5. The capacitive type sensor according to claim 2, wherein the first and second electrodes are joined to the surface of the insulating substrate.

6. The capacitive type sensor according to claim 5, wherein the first and second electrodes are formed by subjecting an electrically conductive substrate, joined to the insulating substrate, to polishing or etching.

7. The capacitive type sensor according to claim 2, wherein
the first electrode comprises a first electrode body and a plurality of first comb-electrode portions extending from the first electrode body;
the second electrode comprises a second electrode body and a plurality of second comb-electrode portions extending from the second electrode body;
the first and second comb-electrode portions are alternately disposed with a predetermined face-to-face distance therebetween; and
the water vapor sensitive film is disposed between and in contact with the first and second comb-electrode portions, and forms a plurality of vertically arranged capacitors with the first and second comb-electrode portions.

8. The capacitive type sensor according to claim 7, further comprising an upper water vapor sensitive film provided on the first and second electrodes and the water vapor sensitive film,
wherein a shielding film is provided in the upper water vapor sensitive film above and near the first and second comb-electrode portions.

9. The capacitive type sensor according to claim 2, wherein:
the first electrode comprises a first electrode body, a first straight electrode portion extending from the first electrode body, and a plurality of first annular electrode portions extending from the first straight electrode portion;
the second electrode comprises a second electrode body, a second straight electrode portion extending from the second electrode body, and a plurality of second annular portions extending from the second straight electrode portion;
the first and second annular electrode portions are coaxially and alternately disposed with a predetermined face-to-face distance therebetween; and
the water vapor sensitive film is disposed between and in contact with the first and second annular electrode portions, and forms a plurality of vertically arranged capacitors with first and second annular electrode portions.

10. The capacitive type sensor according to claim 2, wherein:
the first electrode comprises a first electrode body, at least one first straight electrode portion extending from the first electrode body, and a plurality of first toothed electrode portions extending perpendicularly from the at least one first straight electrode portion;
the second electrode comprises a second electrode body, a plurality of second straight electrode portions extending from the second electrode body, and a plurality of second toothed electrode portions extending perpendicularly from each of the second straight electrode portions;
adjacent ones of the first straight electrode portion, the first toothed electrode portions, the second straight electrode portions, and second toothed electrode portions are disposed to face one another with a predetermined face-to-face distance; and
the water vapor sensitive film is disposed between and in contact with adjacent portions of the first straight electrode portion, the first toothed electrode portions, the second straight electrode portions, and second toothed electrode portions, and forms a plurality of vertically arranged capacitors with the adjacent portions.

11. The capacitive type sensor according to claim 2, wherein:
the first electrode comprises a first electrode body, and a lower electrode portion which extends from the first electrode body and which includes a plurality of first toothed electrode portions disposed at equal intervals;
the first toothed electrode portions extend upward perpendicularly from an upper face of the lower electrode portion to form lower comb electrodes;

the second electrode includes a second electrode body and an upper electrode portion extending from the second electrode body;

the upper electrode portion includes an upper wall having a plurality of second toothed electrode portions disposed at equal intervals, and side walls fixed at bottom faces thereof to the insulating substrate;

the second toothed electrode portions extend downward perpendicular from the upper wall of the upper electrode portion to form upper comb electrodes;

the upper comb electrodes and the lower comb electrodes are disposed to face one another with a predetermined face-to-face distance therebetween; and the water vapor sensitive film is disposed between and in contact with the upper and lower comb electrodes, and forms a plurality of vertically arranged capacitors with the upper and lower comb electrodes.

* * * * *